United States Patent [19]

Clavel et al.

[11] Patent Number: 5,565,689

[45] Date of Patent: Oct. 15, 1996

[54] REACTANT FOR PERFLUOROALKYLATION OF NUCLEOPHILIC SUBSTRATES WITH SODIUM PERFLUOROALKANESULPHINATES IN AN OXIDIZING MEDIUM

[75] Inventors: Jean-Louis Clavel, Ecully; Bernard Langlois, Lyons; Eliane Laurent, Caluire; Nathalie Roidot, Lyons, all of France

[73] Assignee: Rhone-Poulenc Chimie, Courbevoie, France

[21] Appl. No.: 432,031

[22] Filed: May 1, 1995

Related U.S. Application Data

[63] Continuation of Ser. No. 145,651, Oct. 20, 1993, abandoned, which is a continuation of Ser. No. 704,430, May 23, 1991, abandoned.

[30] Foreign Application Priority Data

May 23, 1990 [FR] France .................................. 90 06426

[51] Int. Cl.[6] ..................................... C09K 3/00
[52] U.S. Cl. ................ 252/183.11; 252/182.15; 252/182.3; 252/183.13
[58] Field of Search ........................ 252/182.3, 182.15, 252/183.11, 183.13

[56] References Cited

U.S. PATENT DOCUMENTS

| | | | |
|---|---|---|---|
| 4,304,614 | 12/1981 | Walker et al. ........................ | 149/46 |
| 4,505,929 | 3/1985 | Markley et al. ..................... | 514/520 |
| 4,605,432 | 8/1986 | Adams .................................. | 71/92 |
| 4,863,929 | 9/1989 | Sauer et al. .......................... | 514/288 |
| 4,935,440 | 6/1990 | Muchowski et al. ................ | 514/423 |
| 4,990,699 | 2/1991 | Stahly .................................. | 568/933 |
| 5,041,509 | 8/1991 | Lee et al. ............................. | 526/243 |
| 5,095,136 | 3/1992 | Biller et al. ......................... | 560/124 |
| 5,117,041 | 5/1992 | McBride .............................. | 560/87 |
| 5,153,192 | 10/1992 | Dean et al. .......................... | 544/48 |

OTHER PUBLICATIONS

Hu et al., *Chem. Abs.*, III (7), abs#57023z (1989).

Huang et al., "The Reaction of Perfluoroalkanesulfinates—The Study on Perfluoroalkanesulfinates as Perfluoroalkylation Reagents," Acta Chimica Sinica English Edition, No. 2, Apr., 1989, pp. 190–192.

W. Huang et al. "Perfluoroalkanesulfinates As Perfluoroalkylation Reagents", Chemical Abstracts vol. 112, Abstract No. 112:157603c, Columbus, Ohio & Acta Chim. Sin. (Engl. Ed) 1989, (2) pp. 190–192.

C. Wakselman et al. "Perfluoroalkylation of Anilines In The Presence of Zinc And Sulphur Dioxide", J. Chem. Soc. Comm., No. 22, Nov. 15, 1987, pp. 1701–1703.

*Primary Examiner*—Edward A. Miller
*Attorney, Agent, or Firm*—Finnegan, Henderson, Farabow, Garrett & Dunner, L.L.P.

[57] ABSTRACT

A perfluoroalkylation reactant and a process for its use involving reactions with nucleophilic substrates. The perfluoroalkylation reactant comprises:

a) a perfluoroalkanesulphinate; and, b) a monoelectronic oxidizing system whose redox potential is greater than or equal to 1.20 V relative to the so-called saturated calomel reference electrode (SCE: $Hg/HgCl_2$).

15 Claims, No Drawings

REACTANT FOR PERFLUOROALKYLATION OF NUCLEOPHILIC SUBSTRATES WITH SODIUM PERFLUOROALKANESULPHINATES IN AN OXIDIZING MEDIUM

This application is a continuation of application Ser. No. 08/145,651, filed Oct. 20, 1993, now abandoned which was a continuation of application Ser. No. 07/704,430 filed May 23, 1991, now abandoned.

The present invention relates to a perfluoroalkylation reactant and to a process for the use of this reactant in the perfluoroalkylation of nucleophilic substrates, i.e. those rich in electrons. More particularly, the method of the present invention relates to mono- or polyperfluoroalkylation of electron-rich compounds with a perfluoroalkanesulphinate in an oxidizing medium under mild conditions. The following nonlimiting examples illustrate the wide range of substrates which may be treated by the process of the present invention:

- aliphatic (primary, secondary or tertiary), aromatic or heterocyclic organic sulphides and disulphides,
- thiols,
- olefins and acetylenic compounds which may be activated by electron-donating groups such as enols and their derivatives (in particular enol ethers and esters), enamines and their derivatives, acetylenic ethers, ynamines, etc.
- acrylamides,
- enolisable ketones ($\beta$-diketones, $\beta$-ketoesters),
- ketones or derivatives of $\alpha,\beta$-unsaturated acids, which may be cyclic, such as uracil or uridine,
- aromatic derivatives, preferably substituted by at least one electron-donating group by induction and/or mesomerism, such as toluenes, xylenes, halobenzenes, phenols, anilines and derivatives thereof.

This technique makes it possible to produce, inter alia, perfluoroalkyl thioethers, $\beta,\beta'$,-bis(perfluoroalkyl)-1,2-diols, ketones, $\alpha$-perfluoroalkylated amides or acids, derivatives of $\beta$-perfluoroalkylated enols or perfluoroalkylated aromatic and heterocyclic compounds.

These compounds may be employed as biologically active products or as their precursors. For example, 3-(trifluoromethyl)aniline forms part of the synthesis of the herbicides fluometuron and norflurazon, while 3-(trifluoromethyl)phenol is one of the starting materials for the herbicide diflufenican. Herbicides of the fluothiuron class or the insecticides MB 45950 and MB 46030 (fiprole) contain a trifluoromethyl thioether functional group. The preparation of MB 45950 by this method is described herein.

Trifluoromethylthioacetic acid, which can be made by using the present technique, is an intermediate in the synthesis of the antibiotic cephalosporin cefazaflur (SKF 59962). The corresponding nitrile permits the formation in two stages ("one-pot reaction") of 2-bromo-3-(trifluoromethylthio)pyridine (J. Org. Chem., 1979, 44 (17), 3080). 2,3-Bis(trifluoromethyl)acrylamide, the product of radical trifluoromethylation of acrylamide, is the precursor of 3-(2,2,2-trifluoroethyl) azetidin-2-one, a $\beta$-lactam used for the preparation of antibiotics (Tetrahedron Lett., 1989, 30 (1), 109).

$\alpha,\alpha,\alpha$,-Trifluorothymidine, originating from uridine, is an antiviral compound, and 2-(trifluoromethyl)dopamine or S-(trifluoromethyl)cysteine, resulting from dopamine and from cystine respectively, are enzyme inhibitors (Bull. Chem. Soc. Japan, 1986, 59, 447).

$\omega,\omega,\omega$,-Trifluoromethionine, obtained from homocystine is itself an inhibitor of methionine activation (Can. J. Microbiol., 1986, 12, 143).

Basic treatment of the $\alpha$-(perfluoroalkyl)ketones originating from the present process produces $\alpha,\beta$-unsaturated $\beta$-fluoro-$\beta$-perfluoroalkyl ketones, which are known to be useful dienophiles (Tetrahedron Lett., 1982, 23 (14), 1471). Similarly, $\alpha$-(trifluoromethyl) esters make it possible to obtain $\beta$-difluoroacrylates, which are used in the production of polymers exhibiting excellent mechanical and thermal properties.

Numerous reactants are already in existence and numerous other methods of making perfluoroalkylated compounds and perfluoroalkyl thioethers have been described, either starting with trichloromethylated precursors or trichloromethyl thioethers, or using direct introduction of $C_nF_{2n+1}$ ($R_f$) or $R_fS$ groups. All of them have disadvantages which are mentioned in the review of the prior art which follows.

The fluorination of trichloromethyl groups is described in the following references:

a—M. Hudlicky, "Chemistry of Organic Fluorine Compounds" (2nd edition), pp. 96–106, Ellis Horwood Ltd., Chichester (1976).

b—E. A. Nodiff, S. Lipschutz, P. N. Craig, M. Gordon, J. Org. Chem., 1960, 25, 60.

c—L. M. Yagupolskii, M. S. Marenets, J. Gen. Chem. USSR, 1959, 29 (1), 281.

d—A. Senning, S. O. Lawesson, Acta Chim. Scand., 1962, 16, 117—CA, 57, 7150 h.

e—S.M. Shein, T.V. Kostkina, Yu. P. Melnik, USSR Pat. 163,610 (1964).

f—G. Bulteau, U.S. Pat. No. 3,632,629 (1972)—CA, 76, 112918f.

g—M. Makosza, M. Fedorynski, Synthesis, 1974 (4), 274), which uses the following reaction sequence:

$$R-Y-CH_3 \xrightarrow[\text{initiator}]{X}$$

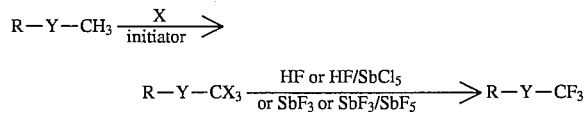

where

Y represents a valency bond, O or S;

X represents Cl or Br (when X represents Br, cf. reference f);

and the initiator is selected from UV light, heat or chemical radical initiators.

This prior art technique is not widely applicable because it requires that the starting methylated substrate be capable of withstanding the radical chlorination and, in particular, does not contain any other $CH_3$ substituent. Fluorination using antimony trifluoride is applicable only in the laboratory and involves major problems in disposing of heavy metals. Fluorination using HF, which is easily capable of being implemented on an industrial scale, nevertheless requires highly specific plants and extreme safety measures. When antimony pentafluoride is to be employed as catalyst, its recovery is difficult or even impossible.

A direct method of fabricating the $SCCl_3$ units from chloroform has been described by reference "g", but this reaction requires that the remainder of the molecule be capable of withstanding the highly basic media. A by-product of this reaction is sodium cyanide, which is highly toxic:

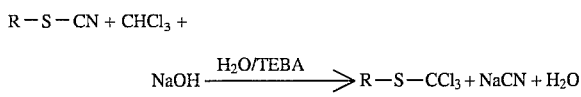

The preparation of $CF_3$ groups by reaction of sulphur tetrafluoride with acids or esters according to the reaction

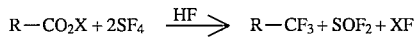

with X=H or alkyl requires the use of highly toxic gaseous $SF_4$ in an anhydrous pressurized hydrofluoric acid medium which is corrosive and toxic. This reaction has been applied to the synthesis of ethyl 3,3,3-trifluoropropanoate from ethyl monomalonate (ref. H. M. Peters, L. O. Ross, R. L. Simon, E. H. Marion, J. Chem. Eng. Data, 1971, 16, 376).

The preparation of $CF_3$ groups by reaction of molybdenum hexafluoride with acids, their chlorides or their esters (ref. M. Van der Puy, J. Fluorine Chem., 1979, 13, 375) uses a relatively unreactive and toxic fluorinating agent which is very expensive, since it is produced by the reaction of molecular fluorine with $MoO_2$. The by-products of this reaction are poorly identified and create serious problems involving the disposal of heavy metals.

Special mention should be made of trifluoromethylations with the aid of bromotrifluoromethane. Bromotrifluoromethane (Halon F 13B1) is a commercial product which is commonly employed as an extinguishing agent in aircraft and computer rooms. It is a trifluoromethylating agent which, however, has the disadvantage of being gaseous ($Bp_{760}=57°$ C.) and of reacting only at a pressure of greater than 3 bars.

Thermal homolysis of $CF_3Br$ requires very high temperatures because of the large energy of the carbon-bromine bond in this reactant. Aromatic compounds are trifluoromethylated thermally by $CF_3Br$ only at 500°–600° C. and under conditions such that the reaction is catalysed with iodine, as disclosed in U.S. Pat. No. 4,038,331 (1975). In the absence of iodine, an aromatic bromination is observed, as disclosed in U.S. Pat. No. 3,890,326 (1973). This method is difficult to extrapolate to an industrial scale. However, when the aromatic substrate is very rich in electrons, a photochemical activation allows trifluoromethylation at room temperature (ref. Shingijutsu Kaihatsu, Jap. J6 1,027,927 (1984).

When the nucleophile itself is not sufficiently reductive, an auxiliary reducing agent is preferably employed to generate the trifluoromethyl radical. This reducing agent may be zinc, copper or the radical-anion of sulphur dioxide, which is obtained from $ZnSO_2$ or alkali metal dithionites or hydroxymethanesulphinates. If the nucleophile is an electronrich aromatic compound, e.g. a compound selected from phenols, anilines, anisoles, pyrrole, etc. (ref. C. Wakselman, M. Tordeux, J. Chem. Soc., Chem. Commun., 1987, 1701), or a disulphide (ref. J. L. Clavel, B. Langlois, M. Tordeux, C. Wakselman (Rhone-Poulenc), Fr. Application 88/16710), the auxiliary reducing agent ($SO_2^-$ or Zn or Cu) can be used in catalytic quantities. The isomer ratio of the trifluoromethylated aromatics is not always satisfactory.

All of these trifluoromethylations, which are conducted in a reducing medium, require that the other substrate groups are not capable of being reduced under the reaction conditions.

A number of methods have been developed which involve starting with perfluoroalkanoic acids or their derivatives which, by themselves, are at least as costly as the corresponding sodium perfluoroalkanesulphinates utilized in accordance with the present invention. The trifluoroacetic derivatives used in the literature, e.g. $CF_3CO_2Na$, $CF_3CO_2Ag$, $(CF_3CO_2)_2Hg$, $CF_3CO_2R$, $CF_3COCl$, $(CF_3CO)_2O$, and $(CF_3CO_2)_2$, are even more costly than $CF_3CO_2H$. These methods employ the electrochemical oxidation of the perfluoroalkanoic acids or the decomposition of some salts (Ag, etc.) or of peroxides.

Therefore, one of the objectives of the present invention is to provide a perfluoroalkylation reactant which is less costly and easier to use than those described above. Another objective of the present invention is to provide a reactant which makes it possible to obtain isomer ratios differing from those obtained with the above reactants.

These objectives and others which will become apparent from the following description can be achieved by means of a perfluoroalkylating reactant comprising:

a) a perfluoroalkanesulphinate, preferably an alkali metal, and more preferably sodium perfluoroalkanesulphinate or an ammonium or phosphonium perfluoroalkanesulphinate; and b) a monoelectronic oxidizing system, i.e. one capable of exchanging only one electron with the reducing system under the conditions of the experiment and such that the potential of the reaction

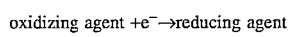

is greater than or equal to 1, preferably to 1.2 V relative to a saturated calomel reference electrode (SCE: $Hg/HgCl_2$).

Oxidizing agents such as $H_2O_2$ by itself, halogens or sodium hypochlorite, which react with $R_fSO_2Na$ by two-electron processes or atomic transfers resulting in $R_fSO_3Na$, are outside the scope of the present invention. However, the hydroxyl radicals generated by $H_2O_2+Fe^{2+}$ (Fenton's reagent) are included within the scope of the present invention.

To determine the most advantageous oxidizing agents, the oxidizing agents may be subjected to a test of oxidation of triflinic acid salt. In this test, a lower yield of triflate anion relative to the triflinic acid salt consumed is indicative of a superior oxidizing agent for use in the present invention. Furthermore, it is preferable that the degree of conversion, or of consumption, of triflinic acid should be high.

Oxidizing agents giving a triflic acid yield (CY) of not more than 1/3, preferably 1/5, and more preferably 1/10, relative to the triflinate consumed, may be considered satisfactory.

Some oxidizing agents react with the species formed. For example, $N_2O_4$ gives trifluoronitrosomethane ($CF_3NO$). Thus, to enable such oxidizing agents to be employed without employing them on themselves, i.e. to avoid reaction with the species formed, substrates which are more reactive than the oxidizing agents are preferably employed.

Suitable oxidizing agents are preferably selected from cerium(IV) ammonium double nitrate, ferric salts, ammonium (or sodium) persulphate or tert-butyl, cumyl or cyclohexyl hydroperoxides. Lead(IV) derivatives and especially its salts such as lead tetraacetate also form part of this class of oxidizing agents. They are, however, more difficult to handle.

The hydroperoxides are preferably activated by catalytic quantities of compounds of molybdenum(VI) ($MoO_2(acac)_2$ or $Mo(CO)_6$), vanadium(V) ($VO(acac)_2$), osmium(VIII) ($OsO_4$) or selenium(IV) ($SeO_2$).

The persulphates are preferably activated by an oxidizable metal salt such as iron(II) (Mohr's salt). An oxidation carrier based on cupric salts, such as, $Cu(acac)_2$ or $(CF_3SO_3)_2Cu$, may be added in catalytic quantities. The oxidation may also take place on the anode of an electrolyser, provided that its potential is suitably chosen. Since it is a liquid, tert-butyl hydroperoxide is particularly preferred.

The perfluoroalkanesulphonate is employed in a proportion of 1 to 7 moles per mole of organic substrate, preferably from 1 to 4 moles/mole. Sodium trifluoromethanesulphinate is particularly preferred as the perfluoroalkanesulphinate.

The oxidizing agents are employed in a proportion of 1 to 10 moles per mole of substrate, preferably from 1 to 7 moles/mole.

The catalysts are added in a proportion of 0.001 to 0.5 moles per mole of substrate, preferably 0.02 to 0.3 moles/mole.

The results are better and more reproducible when the oxidizing agent is introduced slowly into the reaction mixture in a continuous and steady manner, for example with the aid of a syringe pump.

The reaction is usually conducted in aprotic solvents like ethyl acetate or acetonitrile, optionally with the addition of water. However, other solvents such as polar aprotic solvents (dimethylformamide, dimethylacetamide, N-methylpyrrolidone, sulpholane, glymes, hexamethylphosphorotriamide, etc.) or water may be employed provided that they dissolve the sodium perfluoroalkanesulphinate, and preferably the substrate as well, and are insensitive to the action of the perfluoroalkyl radicals and of the oxidizing reactants. From 0.5 to 30 ml of solvent per millimole of substrate, preferably from 1 to 15 ml/mmol, is preferably employed.

The solvent may also consist of excess substrate. The reaction temperature is preferably between 15° and 70° C., and is more preferably between 20° and 50° C. However, lower or higher temperatures can be employed, depending on the reactivity of the substrate. Nevertheless, it is not desirable to exceed 150° C. because the stability of the sodium perfluoroalkanesulphinate decreases above this limit.

The alkali metal perfluoroalkanesulphinates are particularly advantageous perfluoroalkylating reactants insofar as they are conveniently obtained by reaction between a perfluoroalkyl bromide or iodide and a reducing system such as the zinc/sulphur dioxide couple (European Application No. 165,135) or alkali metal dithionites and hydroxymethanesulphinates (European Patent Application Nos. 237,446 and 278,822). In particular, sodium trifluoromethanesulphinate results from the reaction of sodium dithionite with bromotrifluoromethane, an inexpensive commercial product used as an extinguishing gas in aircraft and computer rooms.

The method of the present invention is a mild and rapid trifluoromethylation method which makes it possible, by using a single trifluoromethylating agent (frequently inexpensive, solid, safe and nontoxic) and using oxidizing agents (in particular tBuOOH) which are inexpensive, low in toxicity and relatively nonhazardous, to treat a large number of substrates at atmospheric pressure and room temperature, to produce a wide variety of products of biological interest or of use in the synthesis of new materials. In particular, sodium trifluoromethanesulphinate is easily derived from bromotrifluoromethane and sodium dithionite and is expected to be available on an industrial scale in the near future.

This process is often complementary to trifluoromethylation reactions which utilize $CF_3Br$ in a reducing medium ($Zn$, $Zn/SO_2$, $Na_2S_2O_4$). However, these reactions have the disadvantage of requiring the use of pressurized reactors, of requiring sometimes higher temperature levels and substrates which withstand reducing conditions. The present invention also no longer requires the use of undissolved metals in stoichiometric quantity, which result in abrasion of the reactor, as is the case with the trifluoromethylation of enamines with $CF_3Br+Zn$.

The perfluoroalkanesulphinate preferably has the following formula (I):

$$R-(CF_2)_n-SO_2^- \qquad (I)$$

where R denotes hydrogen, an alkyl group, an aryl group, a chlorine atom, a fluorine atom, or an $SO_2$ group; n denotes an integer from 1 to 8, preferably from 1 to 4. When n is equal to 1, R is preferably fluorine or chlorine.

The term alkyl is used in the widest sense according to the Duval Dictionary of Chemistry. The alkyl group preferably contains not more than 15, and preferably not more than 6 carbon atoms.

The term aryl is defined herein as a mono- or polycyclic aromatic radical, condensed or otherwise, homo- or heterocyclic, optionally substituted, preferably an aromatic radical of not more than 15 carbon atoms, preferably condensed or monocyclic, and optionally substituted.

A second embodiment of the present invention involves a process for perfluoroalkylation of a nucleophilic substrate by contacting the substrate with a reactant comprising:

a) a perfluoroalkanesulphinate, preferably an alkali metal, and more preferably a sodium perfluoroalkanesulphinate, or an ammonium or phosphonium perfluoroalkanesulphinate; and, b) a monoelectronic oxidizing system, i.e. one capable of exchanging only one electron with the reducing system under the conditions of the experiment and such that the potential of the reaction $$\text{oxidizing agent} + e^- \rightarrow \text{reducing agent}$$

is greater than or equal to 1, preferably to 1.2 V relative to a saturated calomel reference electrode (SCE: $Hg/HgCl_2$).

Oxidizing agents such as $H_2O_2$ by itself, halogens or sodium hypochlorite, which react with $R_fSO_2Na$ by two-electron processes or atom transfers resulting in $R_fSO_3Na$, are beyond the scope of the invention. However, the hydroxyl radicals generated by $H_2O_2 + Fe^{2+}$ (Fenton's reagent) are included within the scope of the present invention.

To determine the most advantageous oxidizing agents, the oxidizing agents may be subjected to a test involving the oxidation of triflinic acid salt. In this test, a lower yield of triflate anion relative to the triflinic acid salt consumed is indicative of a superior oxidizing agent for use in the present invention. Furthermore, it is preferable that the degree of conversion, or of consumption, of triflinic acid should be high.

Oxidizing agents giving a triflinic acid yield (CY) of not more than ⅓, preferably ⅕, and more preferably ¹⁄₁₀, relative to the triflinate consumed, may be considered satisfactory.

Some oxidizing agents react with the species formed. For example, $N_2O_4$ gives trifluoronitrosomethane ($CF_3NO$). Thus, to enable such oxidizing agents to be employed without employing them on themselves, i.e. to avoid reaction with the species formed, substrates which are more reactive than the oxidizing agents should be employed.

Sodium trifluoromethanesulphinate or triflinate is particularly preferred as the perfluoroalkanesulphinate.

The class of nucleophilic substrates which give good results is very broad, as illustrated by the list provided above. The process gives particularly advantageous results in the case of aromatic derivatives represented by formula (II):

$$Ar(R)_n \quad (II)$$

in which:

Ar represents a mono- or polycyclic, condensed or otherwise, homo- or heterocyclic aromatic radical, R represents at least one substituent chosen independently from hydrogen, chlorine, bromine, optionally substituted, saturated or unsaturated, linear or branched or cyclic alkyl radicals grafted onto the nucleus so as to avoid the hydrogens in the benzyl position, ether, optionally substituted alkoxy, optionally substituted aryl, aryloxy, amino, hydroxyl, carboxylate, acyloxy, ester, amido and nitrile radicals, n is an integer which is equal to 1, 2, 3 or 4.

In a preferred embodiment:

Ar denotes a monocyclic aromatic radical,

R denotes a donor radical, preferably amino, hydroxyl or alkoxy.

A donor is defined herein as a radical which is a donor because of various effects, e.g. inductive such as silylated compounds ($\sigma_I > 0$), or mesomeric ($\sigma_R \leq 0$). Where there are a plurality of substituents, the overall nucleophilicity of the substrate is preferably similar to or greater than that of benzene.

The following are nonlimiting examples of aromatic derivatives of formula (I) which may be used in the process of the present invention:

benzene, naphthalene, phenanthrene, phenyl ether, biphenyl, bromobenzene, chlorobenzene, ethyl phenylacetate, pyridine, 2-methylpyridine, pyrrole, amines such as aniline, methylanilines, phenoxyanilines, aminonaphthalene, diaminobenzenes, 3-aminopyridine, and phenolic derivatives, examples of which include phenols, cresols, phenylphenols, chlorophenols, aminophenols, anisoles, methoxyphenols, dihydroxybenzenes, 4-tert-butyphenol, 3-tert-butylphenol and 2-hydroxypyridine.

The carbon number is preferably less than or equal to 50, and preferably less than or equal to 30.

The following nonlimiting examples illustrate the invention. In the examples and throughout the specification and claims, all parts and percentages are by weight unless otherwise specified.

In the following examples, DC, RY and CY are defined as:

DC = degree of conversion of the starting material $$DC = \frac{\text{number of moles of starting material converted}}{\text{number of moles of starting material initially present}}$$

RY = yield based on starting material $$RY = \frac{\text{number of moles of final product}}{\text{number of moles of starting material initially present}}$$

CY = yield based on converted material $$CY = \frac{\text{number of moles of final product}}{\text{number of moles of starting material converted}}$$

EXAMPLES

I. Perfluoroalkylation of various substrates.

1—Trifluoromethylation of aliphatic (primary, secondary or tertiary) Qrganic disulphides and of some aromatic or heterocyclic disulphides.

In the examples relating to organic disulphides, the yields will be always expressed in relation to the stoichiometry 1 $RSO_2^-$/1 RSSR.

Example 1

Synthesis of ethyl 3-(trifluoromethylthio)propionate.

The following were introduced successively, with magnetic stirring, into a 100 ml three-necked round bottom flask fitted with a thermometer, a reflux condenser and a system for adding reactants: a solution of 1.86 g ($10 \times 10^{-3}$ mol) of sodium trifluoromethanesulphinate (83.7% purity; impurity: dimethylformamide) in 10 ml of water, 0.09 g ($3 \times 10^{-4}$ mol) of molybdyl bisacetylacetonate $MoO_2(acac)_2$ and a solution of 1.33 g ($5 \times 10^{-3}$ mol) of ethyl 3,3'-dithiodipropionate $(SCH_2CH_2CO_2Et)_2$ in 5 ml of acetonitrile. The resulting mixture was maintained at 18°–20° C. by using a water bath while 2.28 ml of an aqueous solution containing 63% of tert-butyl hydroperoxide ($15 \times 10^{-3}$ mol) were added over 60 min by using a syringe pump. After completion of the addition, the reaction mixture was stirred for 2.5 h at room temperature.

Any excess hydroperoxide was detected by a colorimetric test with potassium iodide and destroyed by the addition of a few drops of a sodium metabisulphite solution. The reaction mixture was then separated and the oil collected was extracted three times with petroleum ether. The ether phases were combined, dried over magnesium sulphate and evaporated. 1.97 g of a yellow liquid were thereby obtained. Its $^{19}F$ NMR spectrum, recorded in the presence of (trifluoromethyl)benzene as an internal standard, shows the formation of $5 \times 10^{-3}$ moles of ethyl 3-(trifluoromethylthio)propionate, which corresponds to a crude yield of 100%. A "sphere-to-sphere" distillation (35° to 50° C., 8.6 hectopascals (hPa)) resulted in the isolation of a pure fraction which was used to provide the following spectroscopic characteristics of the product:

$^1H$ NMR (300 MHz, $CDCl_3$ solvent, TMS reference, δ in ppm): 1.28 (t, J=7 Hz, 3 H); 2.74 (t, J=7 Hz, 2H); 3.12 (t, J=7 Hz, 2 H); 4.18 (q, J=7 Hz, 2 H)

$^{19}F$ NMR (75, 38 MHz, $CDCl_3$ solvent, $CFCl_3$ reference, $\phi_F$ in ppm): −42.16 (s, 3F)

Examples 2 to 13

The same operating procedure as in Example 1 was employed on various substrates except that in some cases tert-butyl hydroperoxide was replaced with potassium persulphate $K_2S_2O_8$ (with the addition of Mohr's salt) or with cerium(IV) ammonium double nitrate (CAN) and in other cases where pure acetonitrile or ethyl acetate were employed as solvents. The results are summarized in Table 1 below:

TABLE 1

R—S—S—R + $CF_3SO_2Na$ + Ox $\xrightarrow[\text{cat.}]{20° C.}$ R—S—$CF_3$
(1 eq.)         (3 eq.)       (2 eq.)

Yield = moles $RSCF_3$/moles RSSR

| Ex. | R | solv. (ml/mmol) subs. | Ox. | cat. (No. of eq.) | Yield (%) |
|---|---|---|---|---|---|
| 2 | $CH_2CH_2E$ | MeCN (1) $H_2O$ (2) | t-BuOOH | — | 73* |
| 3 | " | MeCN (3) | " | — | 71* |

TABLE 1-continued $$\text{R—S—S—R} + \text{CF}_3\text{SO}_2\text{Na} + \text{Ox} \xrightarrow[\text{cat.}]{20°\text{ C.}} \text{R—S—CF}_3$$
(1 eq.) (3 eq.) (2 eq.)

Yield = moles RSCF$_3$/moles RSSR

| Ex. | R | solv. (ml/mmol) subs. | | Ox. | cat. (No. of eq.) | Yield (%) |
|---|---|---|---|---|---|---|
| 4 | " | MeCN | (2.5) | K$_2$S$_2$O$_8$ + Mohr's salt | — | 64 |
|   |   | H$_2$O | (2) |   |   |   |
| 5 | " | MeCN | (1) | CAN | — | 34* |
|   |   | H$_2$O | (2) |   |   |   |
| 6 | CH$_2$E | MeCN | (1.6) | t-BuOOH*** | Mo$^{VI}$ (0.09) | 62 |
|   |   | H$_2$O | (3.3) |   |   |   |
| 7 | n-C$_8$H$_{17}$ | MeCN | (4) | " | — | 96 |
| 8 | " | AcOEt | (4.2) | " | — | 100 |
| 9 | c-C$_6$H$_{11}$ | AcOEt | (3) | " | — | 8* |
| 10 | " | MeCN | (3) | " | — | 45* |
| 11 | t-Bu | " | | " | — | 11 |
| 12 | Het. | MeCN | (3.3) | " | Mo$^{VI}$ (0.04) | 40 |
|   |   | H$_2$O | (3.3) |   |   |   |
| 13 | 4-Cl—Ø | MeCN | (6) | " | Mo$^{VI}$ (0.06) | 32** |
|   |   | H$_2$O | (2) |   |   |   |

Mo$^{VI}$ = MoO$_2$(acac)$_2$
E = CO$_2$Et
Het. = 5-amino-3-cyano-1-(2,6-dichloro-4-trifluoromethyl)-4-pyrazolyl
*yield of isolated product
**by-product: 4-chloro-x-trifluoromethyl-1-(trifluoromethylthio) benzene (2 isomers in a ratio of 1/2): yld = 6%
***introduced manually using dropping funnel.

Example 14

Trifluoromethylation of diphenyl disulphide with sodium trifluoromethanesulphinate and tert-butyl hydroperoxide Example 14a The process of Example 1 was performed, except that the molybdenum catalyst was omitted. The initial quantities used were as follows:

5 mmol of diphenyl disulphide 10 mmol of sodium trifluoromethanesulphinate 10 mmol of water 5 mmol of acetonitrile 15 mmol of tert-butyl hydroperoxide After the usual experimental procedures, a mixture of trifluoromethyl diphenyl disulphide (I) (3 isomers) and trifluoromethyl phenyl sulphide (II) was obtained in a ratio (I)/ (II)=40/60 and a total yield of 12%.

Example 14b

The process of Example 14a was performed, except that pure acetonitrile was used as solvent (4 ml/mmol of substrate). (I) (2 isomers) and (II) were obtained in a 64/36 ratio and a 14% total yield.

Example 14c

The process of Example 14a was performed, except that pure ethyl acetate was used as the solvent (4 ml/mmol of substrate). (I) (3 isomers) and (II) were obtained in a 35/36 ratio and a 34% yield.

3—Trifluoromethylation of 4,4'-dichlorodiphenyl disulphide with sodium trifluoromethanesulphinate in ethyl acetate medium and in the presence of tert-butyl hydroperoxide: Example 15.

The following were introduced successively, with magnetic stirring, into a three-necked round bottom flask fitted with a thermometer, a reflux condenser and a dropping funnel equipped with a needle-valve stopcock:

–1.87 g (12×10$^{-3}$ mol) of sodium trifluoromethanesulphinate in solution at a concentration of 4.6% in ethyl acetate, 0.09 g (3×10$^{-4}$ mol) of MoO$_2$(acac)$_2$, 1.43 g (5×10$^{-3}$ mol) of 4,4'-dichlorodiphenyl disulphide dissolved in 40 ml of ethyl acetate.

The mixture was maintained at 18°–20° C. while 2.28 ml of an aqueous solution containing 63% of tert-butyl hydroperoxide (15×10$^{-3}$ mol) were added over 30 minutes. The reaction mixture was left at room temperature for 2.5 h and was then evaporated. The residue thus obtained was extracted with a water-petroleum ether mixture (50/50) and then extracted three times with pure petroleum ether. The ether phases were combined, dried over magnesium sulphate and evaporated. This yielded a yellow solid containing the starting disulphide and 4-chloro(trifluoromethylthio)benzene in an amount corresponding to a 2% yield. The residue, which was insoluble in water and petroleum ether, consisted of 4-chloro-2-(trifluoromethyl)thiophenol in a quantity corresponding to a 30% yield.

4—Trifluoromethylation of n-octanethiol: Example 16

The method of Example 1 was employed, except that the starting materials were used in the following proportions:

n-octanethiol: 1 eq.

tert-butyl hydroperoxide: 1.5 eq.

sodium trifluoromethanesulphinate: 1 eq.

acetonitrile: 0.5 ml/mmol of substrate.

water: 1 ml/mmol of substrate. Trifluoromethyl n-octyl thioether was obtained in a 12% yield.

5—Trifluoromethylation of aromatic compounds Aromatic compounds were trifluoromethylated with sodium trifluoromethanesulphinate in the presence of tert-butyl hydroperoxide and of cupric trifluoromethanesulphonate in catalytic quantities, according to the general conditions described in Example 1:

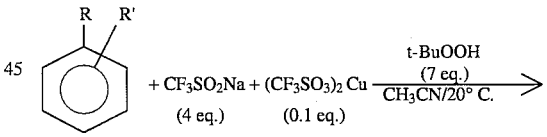

| Ex. | R | R' | MeCN (ml/mmol subs.) | t-BuOOH addition time | Yield |
|---|---|---|---|---|---|
| 17 | OH | H | 3 | 4.5 h | 2-CF$_3$ = 16% |
|   |   |   |   |   | 3-CF$_3$ = 4.6% |
|   |   |   |   |   | 4-CF$_3$ = 24% |
| 18 | 1-OMe | 3-OMe | 4 | 3 h | 2-CF$_3$ = 15% |
|   |   |   |   |   | 6-CF$_3$ = 59% |

The trifluoromethylation products of phenol were identified in the crude reaction mixture by comparison of their $^1$H and $^{19}$F NMR spectra with those of commercial isomeric trifluoromethylphenols, and were quantified using $^{19}$F NMR in the presence of (trifluoromethyl) benzene as internal standard. The trifluoromethylation products 1,3-dimethoxybenzene were separated, isolated and characterized spectroscopically and by their elemental analysis.

6—Trifluoromethylation of enol acetates Isopropenyl acetate and the enol acetate corresponding to 6-undecanone were treated with sodium trifluoromethanesulphinate and tert-butyl hydroperoxide in acetonitrile and in the presence of catalytic quantities of cupric trifluoromethanesulphonate, in the same way as the above aromatic compounds.

Example 19

Trifluoromethylation of isopropenyl acetate

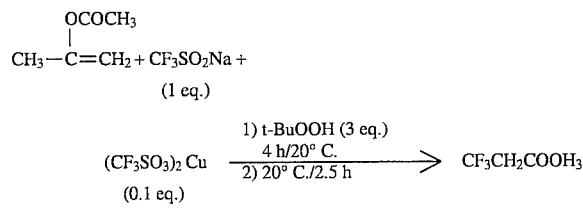

The acetonitrile solvent was employed in a proportion of 1.5 ml/mmol of isopropenyl acetate.

The $^1$H and $^{19}$F NMR spectra of the final reaction mixture, in the presence of (trifluoromethyl) benzene used as an internal standard, reveal the formation of 4,4,4-trifluoro-2-butanone in a 53% yield. This relatively volatile product was isolated in the form of the corresponding pure 2,4-dinitrophenylhydrazone, which was characterized by its $^1$H and $^{19}$F NMR spectra, its mass spectrum and its elemental analysis.

Example 20

Trifluoromethylation of the enol acetate of 6-undecanone.

The reaction was carried out in the same way as in Example 19 by starting with 4 equivalents of tert-butyl hydroperoxide, 2 equivalents of sodium trifluoromethanesulphinate, 0.25 equivalents of cupric trifluoromethanesulphonate and 3 ml of acetonitrile per mmol of substrate. The addition time of the aqueous solution containing 63% hydroperoxide was 2.75 h. After the usual treatment, a mixture of racemic 5-(trifluoromethyl)-6-undecanone (yield=3%) and of two E and Z isomers of 6-acetoxy-7-(trifluoromethyl)-5-undecene (yields=23% and 2%) was isolated. After hydrolysis, this mixture yielded pure 5-(trifluoromethyl)- 6-undecanone.

Example 21

Trifluoromethylation of the enol acetate of 6-undecanone in the presence of sodium acetate.

The reaction was carried out in the same way as in Example 20 by starting with 2 equivalents of tert-butyl hydroperoxide, 4 equivalents of sodium trifluoromethanesulphinate, 0.25 equivalents of cupric trifluoromethanesulphonate, 1 equivalent of sodium acetate and 3 ml of acetonitrile per mmol of substrate. After the usual treatment, an equimolar mixture of the E and Z isomers of 6-acetoxy-7-(trifluoromethyl)-5-undecene was isolated.

Example 22

Trifluoromethylation of 4-hydroxy-6-(methyl)-2-pyranone.

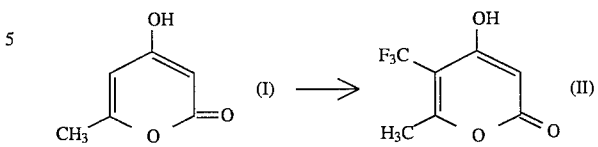

The reaction was carried out in the same way as in Example 19 by starting with 4 equivalents of sodium trifluoromethanesulphinate, 7 equivalents of tert-butyl hydroperoxide, 0.1 equivalents of cupric trifluoromethanesulphonate and 4 ml of acetonitrile per mmol of substrate. The addition time of tert-butyl hydroperoxide was 3.75 h. After the usual treatment, the product (II) was collected in the form of an isomerically pure solid characterized by its $^1$H and $^{19}$F NMR spectra, its mass spectrum and its elemental analysis. The yield of isolated product was 45%.

Example 23

S-Trifluoromethylation of (L)-cystine dimethyl ester N,N'-bishydrochloride.

The reaction was performed as in Example 1, starting from 4.4 mmol of substrate, 13.3 mmol of sodium trifluoromethanesulphinate, 0.294 mmol of $MoO_2(acac)_2$, 19.7 mmol of tert-butyl hydroperoxide and 70 ml of water. The hydroperoxide was added over 2 h and the mixture, after standing at room temperature with stirring for 2 h, was extracted with 3×30 ml of diethyl ether. The aqueous phase was then neutralized to pH=10 and extracted again with 3×30 ml of diethyl ether. The ether solution was treated with 4.55 mmol of hydrochloric acid and 0.5 g of S-trifluoromethyl-(L)-cysteine methyl ester N-hydrochloride was filtered off (47% yield). The product was characterized by its $_1$H NMR ($D_2O$, TMS) spectrum (3.6 ppm (m, 2H), 3.85 ppm (s, 3H), 4.55 ppm (m,1H) 5.65 ppm (s, 3H)), its $^{19}$F NMR (DMSO, $CFCl_3$) spectrum (s,–43.9 ppm (DMSO, $CFCl_3$)) and its $[\alpha]$ $D^{25}$=+11.69 (MeOH, c=0.992 g/100 ml).

Example 24

S-Trifluoromethylation Of N,N'-diacetyl (L)-cystine dimethyl ester.

The reaction was performed as in Example 23, starting from 2.4 mmol of substrate, 4.82 mmol of sodium trifluoromethanesulphonate, 7.2 mmol of tert-butyl hydroperoxide, 0.144 mmol of $MoO_2(acac)_2$ and 50 mml of acetonitrile as a solvent. The reaction mixture was poured into 100 ml of water and extracted with 50+20 ml of diethyl ether. Evaporation yields 0.588 g of a crude product which was subjected to chromatography on silica with an acetone-petroleum ether mixture (40/60). 0.29 g of S-trifluoromethyl-N,N'-diacetyl (L)-cysteine methyl ester was thus recovered (yield=46%, purity=94%). After recrystallization from cyclohexane, the product was characterized by its $^1$H NMR ($D_2O$, TMS) spectrum: 2.0 ppm (s,3H), 3.4 ppm (m, 2H), 3.85 ppm (s, 3H), 4.95 ppm (m, 1H) 6.75 ppm (m, 1H)), its $^{19}$F NMR ($D_2O$, $CFCl_3$) spectrum (s,–41.1 ppm (DMSO, $CFCl_3$)) and its $[\alpha]D^{25}$=+41.15 (MeOH, c=1.152 g/100 ml).

Example 25

S-Trifluoromethylation of (D,L)-homocystine dimethyl ester N,N'-bisydrochloride.

The process of Example 23 was performed, starting from 2.7 mmol of substrate, 5.4 mmol of sodium trifluoromethanesulphinate, 8.12 mmol of tert-butyl hydroperoxide, 0.162 mmol of $MoO_2$ $(acac)_2$ and 60 ml of water as solvent. After the usual experimental procedures, 0.38 g of pure S-trifluoromethyl-(D,L)-homocysteine methyl ester N-hydrochloride was recovered and characterized by its $^1H$ NMR ($D_2O$, TMS) spectrum (2.45 ppm (m, 2H), 3.15 ppm (m, 2H), 3.85 ppm (s, 3H), 4.3 ppm (m, 1H), 4.80 ppm (s, 3H)) and its $^{19}F$ NMR ($D_2O$, $CFCl_3$) spectrum (s,–4.8 ppm).

Example 26

S-Trifluoromethylation of N,N'-diacetyl-(D,L)-homocystine dimethyl ester.

The process of Example 24 was performed, starting from 2.34 mmol of substrate, 4.68 mmol of sodium trifluoromethanesulphinate, 7.23 mmol of tert-butyl hydroperoxide, 0.14 mmo of $MoO_2(acac)_2$ and 60 ml of acetonitrile. Chromatography was performed with a 50/50 acetone-petroleum ether mixture. 90% pure S-trifluoromethyl-N-acetyl-(D,L)-homocysteine methyl ester was recovered (yield=37%). $^1H$ NMR ($DCDl_3$, TMS): 1.9 ppm (s, 3H), 2.1 ppm (m, 2H), 2.85 (m, 2H, 3.65 ppm (s, 3H), 4.65 ppm (m, 1H), 7.0 ppm (m, 1H). $^{19}F$ NMR ($CDCl_3$, $CFCl_3$):–42.1 ppm (s)

Example 27

Trifluoromethyl n-octyl sulphide from 4-nitrophenyl n-octyl disulphide.

Using the method of Example 14b, 3.13 mmol of 4-nitrophenyl n-octyl disulphide and 6.25 mmol of sodium trifluoromethanesulphinate in 20 ml acetonitrile were treated with 9.39 mmol of tert-butyl hydroperoxide. Trifluoromethyl n-octyl sulphide, characterized by its $^1H$ and $^{19}F$ NMR spectra, was isolated after chromatography on silica with petroleum ether. The yield was 22%.

Example 28

Trifluoromethylation of methyl 4-hydroxybenzoate.

When this substrate was reacted under the conditions described in Example 17, methyl 3-trifluoromethyl-4-hydroxybenzoate was obtained in a 19% yield, after chromatography on silica with a 30/70 diethyl ether-petroleum ether mixture. $^1H$ NMR ($CDCl_3$, TMS): 3.9 ppm (s, 3H), 7.0 ppm (d, 1H, J=8 Hz), 8.0 ppm (dd, 1H), 8.15 ppm (d, 1H, J=2 Hz), 9.7 ppm (m, 1H). $^{19}F$ NMR ($CDCl_3$, $CFCl_3$):–63.3 ppm.

Example 29

Trifluoromethvlation of acetanilide.

1.35 g (10 mmol) of acetanilide, 6.56 g (40 mmol) of sodium trifluoromethanesulphinate, 0.3615 g (1 mmol) of cupric trifluoromethanesulphonate, 20 ml of acetonitrile and 40 ml of water were placed in a three-necked vessel fitted with a thermometer, a reflux condenser and a magnetic stirrer. 10.64 ml of a 63% aqueous solution of tert-butyl hydroperoxide (70 mmol) were introduced, at 18°–20° C. over 4 h 40 min, by means of a syringe pump. The reaction mixture was then allowed to stand at room temperature for 2.5 h. The excess hydroperoxide, detected by an iodide test, was destroyed with aqueous sodium metabisulphite. After dilution with 40 ml of water, the mixture was extracted with 3×40 ml of diethyl ether. The ether solution was evaporated. The residue was examined by $^{19}F$ NMR ($CDCl_3$, $CFCl_3$) in the presence of 2,2,2-trifluoroethanol as internal standard.

The spectra were compared with those of authentic samples of trifluoromethylated acetanilides prepared by acetylation of commercial ortho, meta and para trifluoromethylanilines. The yields were as follows:

| 2-$CF_3$ acetanilide | 30% yield | –61.32 ppm |
|---|---|---|
| 3-$CF_3$ acetanilide | 7% yield | –63.07 ppm |
| 4-$CF_3$ acetanilide | 14.5% yield | –62.43 ppm |

Example 30

Trifluoromethylation of aniline.

This substrate was subjected to the conditions described in Example 29 using the same procedure, the same amounts of starting materials, and the same analysis. The $^{19}F$ NMR spectrum indicates the formation of two isomeric trifluoromethylanilines (–61.25 and –63.85 ppm) with a total yield of 10%.

Example 31

Trifluoromethylation of 2,6-dichloroaniline.

This substrate was treated under the same conditions as acetanilide (Example 29) (Ar—$NH_2$/$CF_3SO_2Na$/$(CF_3SO_3)_2Cu$/t-BuOOH=1/ 4/0.1/7), either in a water-acetonitrile mixture (4 and 2 ml/mmol of substrate) or in pure acetonitrile (6 ml/mmol of substrate). Two isomeric trifluoromethylated 2,6-dichloroanilines, characterized by their $^{19}F$ NMR spectra ($CDCl_3$, $CFCl_3$), were obtained. Their yields were dependent on the nature of the solvent. The yields are as follows:

| solvent | (I) (–61.97 ppm) | (II) (–63.08 ppm) |
|---|---|---|
| MeCN—$H_2O$ | 11% | 4% |
| MeCN | 22% | 7% |

Example 32

Trifluoromethylation of N-acetylpyrrole.

N-Acetylpyrrole, dissolved in pure acetonitrile (6 mml/mmol), was subjected to the same conditions as acetanilide (substrate/$CF_3S0_2Na$/$(CF_3SO_3)_2Cu$/t-BuOOH=1/4/0.1/7), as disclosed in Example 29. The residue was purified by chromatography on silica with a diethyl ether-petroleum ether mixture (20/80). Pure 2-trifluoromethyl-N-acetylpyrrole was isolated in a 35% yield.

$^1HNMR$ ($CDCl_3$, TMS): 2.6 ppm (s, 3H), 6.3 ppm (m, $^1H$), 6.9 ppm (m, $^1H$), 7.4 ppm (m, $^1H$)

$^{19}F$ NMR ($CDCl_3$, $CFCl_3$):–59.42 ppm (s)

Example 33

Trifluoromethylation of 1,3-dimethoxybenzene in the absence of cupric species.

1,3-Dimethoxybenzene was reacted under the conditions reported in Example 18, except that cupric trifluoromethanesulphonate was omitted. Four trifluoromethylated 1,3-dimethoxybenzenes were detected by $^{19}F$ NMR:

| 4-$CF_3$-1,3-$(OMe)_2$—$C_6H_3$ | (I) | yield = 20% |
|---|---|---|
| 2-$CF_3$-1,3-$(OMe)_2$—$C_6H_3$ | (II) | yield = 7.5% |
| 4,6-$(CF_3)_2$-1,3-$(OMe)_2$—$C_6H_2$ | (III) | yield = 23% |
| 2,6-$(CF_3)_2$-1,3-$(OMe)_2$—$C_6H_2$ | (IV) | yield = 7.5% |

The mixture of (I)+(II)+(IV) was isolated from the reaction residue by chromatography on silica ($Et_2O$/petroleum ether=3/247) and (III) was eluted in a pure form with $Et_2O$/petroleum ether=5/ 245. (I), (II) and (III) were then separated by preparative VPC (Carbowax 20M on Chromosorb WAW DMS, ⅜", 3 meters). All the isolated compounds were analyzed by $^1$H NMR, $^{19}$F NMR and mass spectrometry.

$^1$H NMR (CDCl$_3$, TMS):

(I): 7.470 ppm (d, 1H, J=8.5 Hz), 6.497–7.255 ppm (m, 2H), 3.867 ppm (s, 3H), 3.836 ppm (s, 3H)

(II): 7.384 ppm (t, 1H, J=8.5 Hz), 6.611 ppm (d, 2H, J=8.5 Hz), 3.862 ppm (s, 6H)

(III): 7.7 ppm (s, 1H), 6.5 ppm (s, 1H), 3.9 ppm (s, 6H)

(IV): 7.722 ppm (d, 1H, J=8.5 Hz), 6,829 ppm (d, 1H, J=9.0 Hz), 3.942 ppm (s, 3H), 3.890 ppm (s, 3H) $^{19}$F NMR (CDCl$_3$, CFCl$_3$):

(I):–61,974 ppm (s)

(II):–55,498 ppm (s)

(III):–62.3 ppm (s)

(IV):–57,766 ppm (s),–60,939 ppm (s)

II Test for choosing the oxidizing agents

The following examples of oxidizing agents were tested to demonstrate the value of the test for choosing the oxidizing agents.

II.1 OXIDATION WITH AIR

The reaction was carried out at atmospheric pressure in a cylindrical reactor fitted with a magnetic turbine serving to recycle the reaction liquid by means of a side tube, a quartz-jacketed central tube immersed within the reactor, enabling the reaction mixture to be irradiated and a Teflon dip-tube connected to compressed air. On top of the assembly, a reflux condenser was connected to a bubble counter. All the tests were carried out at room temperature (approximately 25° C.). If necessary, N$_2$O$_4$ was introduced as a solution in carbon tetrachloride (approximately 1 g in 50 g of CCl$_4$).

The operating conditions are summarized in the table below:

| SOLVENT | CATALYST | TIME hours | DC CF$_3$SO$_2$— (%) | CY CF$_3$SO$_3$— (%) |
|---|---|---|---|---|
| acetone/CCl$_4$ | N$_2$O$_4$ + hνl | 5 | 98.5 | 27 |
| acetone | Cu(II)** + hνl | 4 | 6 | 21.7 |
| acetone/CCl$_4$ | N$_2$O$_4$ | 3 h 30 | 92.7 | 12.2 |

νl: 254 nm - quartz-jacketed low-pressure mercury vapor lamp.
**: Cu(II) introduced in the form of octoate.

II.2 Oxidation with oxygen

The reaction was carried out in a 400-ml reactor (Teflon FEP-coated stainless steel). The absolute oxygen pressure was approximately 13×10$^4$Pa.

The pressure was controlled by Logilap hardware and a mass-flowmeter in combination with an integrating unit which allows the oxygen flow to be measured and integrated as a function of time.

Various catalysts were employed in combination with various solvents, as shown in the following table.

| SOLVENT | CATALYST | T °C. | TIME hours | DC CF$_3$SO$_2$— (%) | CY CF$_3$SO$_3$— (%) |
|---|---|---|---|---|---|
| AcOEt | Cu(II)/hν*** | 50° C. | 10 | 10.3 | 46 |
| Water | H$^+$/Cu(II)** | 50° C. | 7.30 | 92.1 | 13.9 |
| Acetone | Cu(II)** | 40° C. | 13 | 12.3 | 50 |
| Acetone | Cu(II)** | 25° C. | 5 | 9.0 | 44.4 |
| Acetonitrile | Cu(AcAc)$_2$ | 40° C. | 2.45 | 21.1 | 52.4 |

**: Cu(II) introduced as copper octoate
Co(II) introduced as cobalt acetate
***: reaction at atmospheric pressure in a glass reactor.

From the above-described results it was concluded that the test in the presence of H$^+$ was not meaningful because the decomposition was not an oxidation.

II.3 Oxidation with N$_2$O$_4$

In the above tests involving oxidation with air, N$_2$O$_4$ was used as a catalyst. It was also tested as a stoichiometric oxidizing agent. In this test, a solution of N$_2$O$_4$ in carbon tetrachloride was poured into a suspension of CF$_3$SO$_2$Na in CCl$_4$. The reaction took place at a temperature of between 5° C. and 10° C. A release of blue-colored gas was observed which was sufficiently characteristic to suggest the presence of trifluoronitrosomethane. IR analysis enables the presence of CF$_3$NO in this gas to be confirmed.

Ion chromatography analysis of the salts remaining in the reaction mixture after the solvent (CCl$_4$) was removed is as follows:

—CF$_3$SO$_2$Na 0%

—CF$_3$SO$_3$Na 7% (presently initially)

—NaHSO$_3$ 65%

—NaF 6.8%

A monoelectronic oxidation according to the invention was involved here, which is indicated here by th presence of NaHSO$_3$. The NO reducing agent acts as a nucleophile.

II.4 Oxidation with hydroperoxides

These experiments were carried out in a 250-ml three-necked round bottom flask with central stirring, supporting a dropping funnel, a thermometer jacket and a reflux condenser. They are summarized in the following table:

| SOLVENT | OXIDIZING AGENTS | CATALYSTS | T (°C.) | TEST TIME (h) | DC →\| CF$_3$SO$_2$— (%) | CY →\| CF$_3$SO$_3$— (%) |
|---|---|---|---|---|---|---|
| Acetone | CHP | VO(AcAc)$_2$ | 25°–50° | 6 | 95 | 8 |
| Ethyl ac. | CHHP | MoO$_2$(AcAc)$_2$ | 0°–5° | 4 | 100 | 0 |
| Water | t-BuOOH | MoO$_2$(AcAc)$_2$ | 0°–5° | 2 | 91.5 | 15.3 |
| Ethyl ac. | t-BuOOH | MoO$_2$(AcAc)$_2$ | 25° | 2 | 100 | 0.1 |

CHP = cumyl hydroperoxide; CHHP — cyclohexyl hydroperoxide

The results indicate the predominant scission of the carbon-sulphur bond (CY>90%). In these tests, sodium hydrogen sulphite was again found among the residual salts. Relatively little fluoride was found.

II.5 Oxidation with aqueous bleach or aqueous hydrogen peroxide

The experiment was carried out in the same apparatus as that described in the preceding section. During the test with aqueous bleach a large excess of the latter was employed (aqueous bleach containing 15% of active chlorine). The reaction was mildly exothermic. The temperature rose from 22.4° to 28.3° C. over 1 hour. The results of the chromatographic analysis were as follows: DC $CF_3SO_2Na$=43.4%, CY $CF_3SO_3Na$=91%

In the experiments involving 30% strength aqueous hydrogen peroxide, 6 times the stoichiometric quantity, relative to $CF_3SO_2Na$, was employed. The reaction was highly exothermic. After 6 hours' reaction at a temperature of between 0° C. and 25° C., the degree of conversion of $CF_3SO_2Na$ was 100% and the $CF_3SO_3Na$ yield (RY) was 96%. No fluoride was detected.

In this experiment, the homolytic scission did not take place. Transfers of matter in favor of the triflinate took place to give triflate.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What I claim is:

1. A composition useful as a perfluoroalkylation reactant, said composition comprising:
    a) an optionally substituted perfluoroalkanesulphinate represented by formula I:

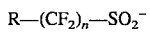
    $$R\text{—}(CF_2)_n\text{—}SO_2^- \qquad I$$

wherein R represents hydrogen, an alkyl group, an aryl group, a chlorine atom, a fluorine atom, or an $SO_2$ group; and n represents an integer from 1 to 8;
    b) an oxidizing agent that will give a triflic acid yield of not more than ⅓ relative to triflinate consumed; and
    c) a catalyst effective to activate said oxidizing agent wherein said catalyst is a catalyst salt of an oxidizable metal or a molybdenum compound, a vanadium compound, an osmium compound, or a selenium compound.

2. The composition of claim 1, wherein said optionally substituted perfluoroalkanesulphinate represented by formula I is an optionally substituted alkali metal perfluoroalkanesulphinate.

3. The composition of claim 2, wherein said alkali metal is sodium.

4. The composition of claim 1, wherein said oxidizing agent is selected from cerium (IV) ammonium double nitrate, a ferric salt, ammonium persulphate, sodium persulphate, tert-butyl hydroperoxide, cumyl hydroperoxide, and cyclohexyl hydroperoxide.

5. The composition of claim 1, wherein n is 1.

6. The composition of claim 1, wherein said optionally substituted perfluoroalkanesulphinate is sodium trifluoromethane sulphinate.

7. The composition of claim 1, wherein said oxidizing agent is a persulphate, a hydroperoxide, or a hydorxyl radical generated by a Fenton reagent.

8. The composition according to claim 7, wherein said Fenton reagent is $H_2O_2+Fe^{2+}$.

9. The composition of claim 1, wherein said optionally substituted perfluoroalkanesulphinate is an ammonium perfluoroalkanesulphinate or a phosphonium perfluoroalkanesulphinate.

10. The composition of claim 1, wherein said oxidizing agent will give a triflic acid yield of not more than ⅓ relative to triflinate consumed.

11. The composition of claim 1, wherein said oxidizing agent will five a triflic acid yield of not more than ¹⁄₁₀ relative to triflinate consumed.

12. The composition of claim 1, wherein said catalyst is $MoO_2(acac)_2$, $Mo(CO)_6$, $VO(acac)_2$, $OsO_4$, or $SeO_2$.

13. The composition of claim 1, wherein said oxidizing agent is a persulphate and said catalyst is a salt of an oxidizable metal.

14. The composition of claim 1, wherein said oxidizing agent is a hydroperoxide and said catalyst is a compound of molybdenum (VI), vanadium (V), osmium (VIII), or selenium (IV).

15. A composition useful as a perfluoroalkylation reactant, said composition comprising:
    a) an optionally substitututed perfluoroalkanesulphinate represented by formula I:

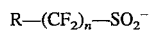
    $$R\text{—}(CF_2)_n\text{—}SO_2^- \qquad I$$

wherein R represents hydrogen, an alkyl group, an aryl group, a chlorine atom, a fluorine atom, or an $SO_2$ group; and n represents an integer from 1 to 8;
    b) an oxidizing agent selected from the group consisting of a persulphate, a hydroperoxide, and a hydroxyl radical generated by a Fenton reagent; and
    c) a catalyst effective to activate said oxidizing agent wherein said catalyst is catalyst salt of an oxidizable metal or a molybdenum compound, a vanadium compound, an osmium compound, or a selenium compound.

* * * * *

UNITED STATES PATENT AND TRADEMARK OFFICE
CERTIFICATE OF CORRECTION

PATENT NO. : 5,565,689
DATED : October 15, 1996
INVENTOR(S) : Jean-Louis CLAVEL et al.

It is certified that error appears in the above-indentified patent and that said Letters Patent is hereby corrected as shown below:

Claim 7, column 18, line 11, "hydorxyl" should read --hydroxyl--.

Claim 11, column 18, line 22, "five" should read --give--.

Claim 15, column 18, line 47, before "catalyst salt" insert --a--.

Signed and Sealed this

Eleventh Day of February, 1997

Attest:

BRUCE LEHMAN

Attesting Officer

Commissioner of Patents and Trademarks